United States Patent [19]

Tsujikawa et al.

[11] Patent Number: 5,178,610
[45] Date of Patent: Jan. 12, 1993

[54] LIQUID INFUSION DEVICE

[75] Inventors: Hajime Tsujikawa, Otsu; Katsuhiro Hiejima, Kusatsu, both of Japan

[73] Assignee: Nissho Corporation, Osaka, Japan

[21] Appl. No.: 723,886

[22] Filed: Jul. 1, 1991

[30] Foreign Application Priority Data

Jul. 5, 1990 [JP] Japan .................................. 2-178964
Aug. 11, 1990 [JP] Japan .................................. 2-211789

[51] Int. Cl.⁵ .......................................... A61M 37/00
[52] U.S. Cl. ............................ 604/132; 128/DIG. 12
[58] Field of Search .......................... 604/132, 131, 93; 128/DIG. 12

[56] References Cited

U.S. PATENT DOCUMENTS 3,961,725 6/1976 Clark .
4,386,929 6/1983 Peery et al. .
4,909,790 3/1990 Tsujikawa .......................... 604/132

FOREIGN PATENT DOCUMENTS 0295504 12/1988 European Pat. Off. ............ 604/131
3618739 12/1986 Fed. Rep. of Germany ... 128/DIG. 12

Primary Examiner—Gene Mancene
Assistant Examiner—Jeffrey A. Smith
Attorney, Agent, or Firm—Armstrong, Westerman, Hattori, McLeland & Naughton

[57] ABSTRACT

A liquid infusion device comprising a bladder assembly, an approximately tubular housing, and a liquid-drug-dispensing portion. The bladder assembly comprises a rod-like inner shaft, a tubular outer shaft slidably encasing the inner shaft, an inner shaft supporter, and a bladder made of elastic material and placed outside two shafts. The housing contains the bladder assembly and has an inlet/outlet portion at an end of the housing. The inner shaft supporter has at least one port for liquid drug communicating with the inlet/outlet portion. An amount of liquid drug remaining in the bladder can be greatly reduced, since a clearance between the inner shaft and outer shaft can be made very small.

6 Claims, 9 Drawing Sheets

LIQUID INFUSION DEVICE

BACKGROUND OF THE INVENTION

The present invention relates to a liquid infusion device used for continuously dispensing a predetermined amount of liquid drug little by little to blood vessel, extradural space, subctis, urinary bladder and the like, and more particularly to a liquid infusion device capable of minimizing liquid drug remaining in a bladder, whereby effectively utilizing liquid drug without waste.

Hitherto, as a device for dispensing a very small amount of liquid drug such as antibiotics and carcinostatic substance to blood vessel, urinary bladder and the like, there has been used an infusor of liquid drug with a bladder wherein liquid drug is charged into the bladder made of elastic material and liquid drug is dispensed into blood vessel and the like for a relatively long period of time with the use of shrinkage force of the bladder. The present applicant proposed a liquid infusion device which was improved from a viewpoint of prevention of leakage of liquid drug and prevention of contamination of bacteria and the like into liquid drug (Japanese Unexamined Patent Publication No. 135360/1989).

The liquid infusion device described in the above publication comprises, as shown in FIGS. 10 and 11, a bladder assembly a, a housing b for containing the bladder assembly a, a flow-regulating portion c having an injection needle 130 and a pipe 131 with small holes. The bladder assembly a comprises, as shown in FIG. 11, a tubular outer shaft 132, an inner shaft 133 slidably received within the outer shaft 132, a bladder 134 made of elastic material and placed outside the outer shaft and inner shaft wherein one end of the bladder is tightly fixed to the outer shaft 132 and the other end of the bladder is tightly fixed to the inner shaft 133, and a plug for injecting liquid drug into the bladder provided in the end portion of the outer shaft 132 opposite to the end whereinto the inner shaft 133 is inserted.

In using the above-mentioned liquid infusion device, the plug 135 is pricked with an injection needle of an injector, and liquid drug is charged into the bladder 134. After a predetermined amount of liquid drug is charged into the bladder 134, the injector is pulled out from the plug 135. Then, the plug 135 is pricked with the injection needle 130 of the flow-regulating portion c. The dispensation of liquid drug into the body of a human patient is carried out after prescribed operation such as air venting.

According to the liquid infusion device described in the above-mentioned publication, a closed-type housing is used so that superior effects such as prevention of leakage of liquid drug even if the bladder is broken can be obtained. However, a certain degree of clearance is required between the inner surface of an outer shaft and the outer surface of an inner shaft, because liquid drug is designed to flow out from an end of the outer shaft and therefore the inside of the outer shaft functions as not only moving space of the inner shaft but also passage of liquid drug. Accordingly, there is a problem that a certain degree of liquid drug remains within the outer shaft after the bladder perfectly shrinks. When using expensive liquid drug such as morphine hydrochloride and carcinostatic substance, a large amount of remaining liquid drug becomes a serious problem economically. Therefore, it has been desired to reduce the amount of remaining liquid drug as much as possible in the bladder.

The present invention was made to solve the drawbacks of the conventional liquid infusion device mentioned above, and it is an object of the present invention to provide a liquid infusion device capable of greatly reducing the amount of liquid drug remaining in the bladder.

SUMMARY OF THE INVENTION

In accordance with the present invention, there is provided a liquid infusion device comprising (a) a bladder assembly comprising a bar-like inner shaft, a tubular outer shaft slidably encasing the inner shaft, an inner shaft supporter integrally formed with the inner shaft at one end of the inner shaft on the opposite side from the outer shaft side, and a bladder made of elastic material and placed outside the outer shaft and inner shaft wherein one end of the bladder is tightly fixed to the outer shaft and the other end of the bladder is tightly fixed to the inner shaft, (b) an approximately tubular housing containing the bladder assembly and having an inlet/outlet portion of liquid drug at an end of the housing, (c) a liquid-drug-dispensing portion connected to the inlet/outlet portion and having a flow-regulating portion for regulating a flow rate of liquid drug wherein the inner shaft supporter has at least one port for liquid drug communicating with the inlet/outlet portion.

DETAILED DESCRIPTION

Next, a liquid infusion device of the present invention is explained in detail based on the accompanying drawings.

Figure 1:
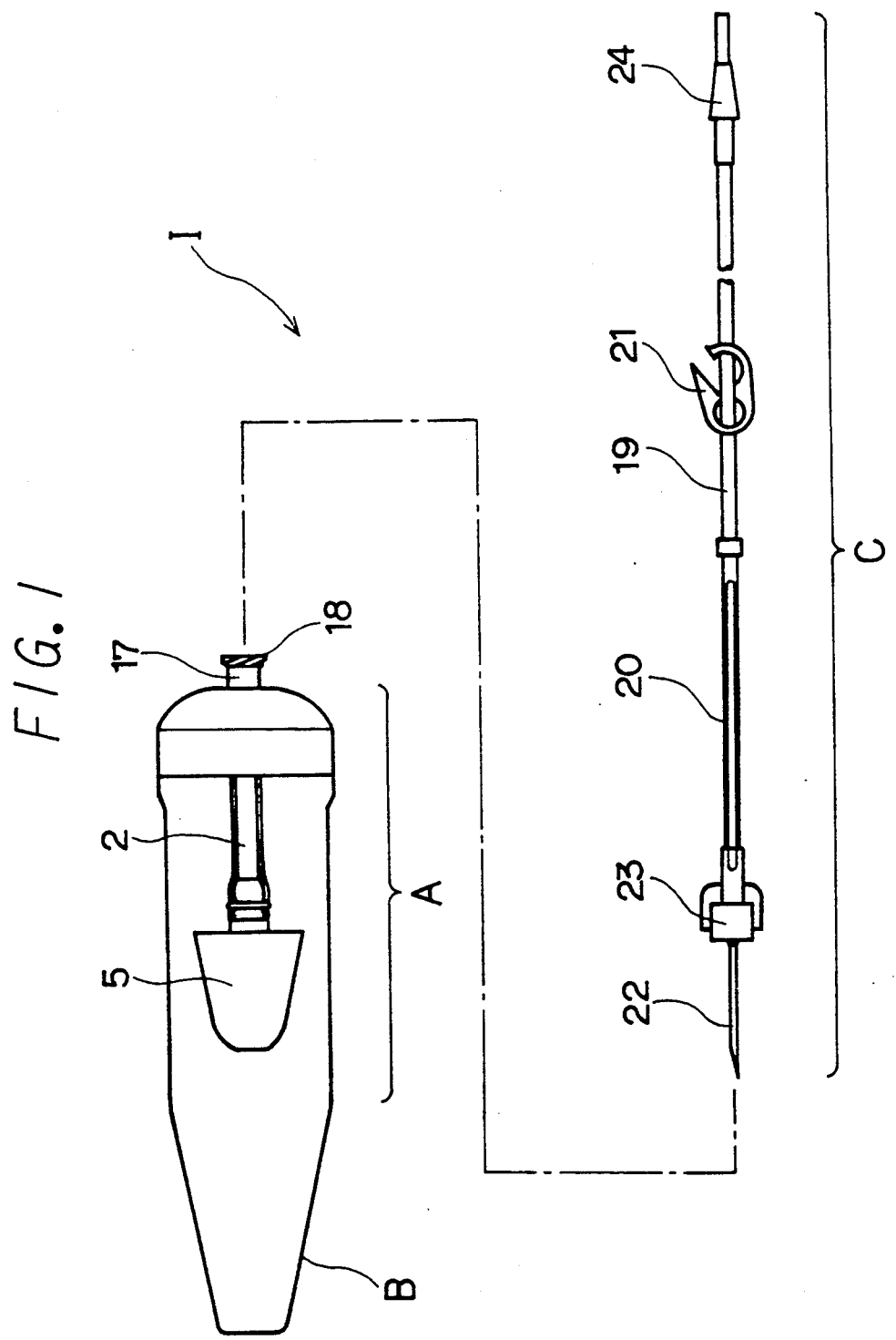
FIG. 1 is an explanatory view of an embodiment of a liquid infusion device of the present invention wherein an injection needle is not pricked into an injection plug.

In FIG. 1, I is an embodiment of a liquid infusion device of the present invention. The liquid infusion device I comprises a bladder assembly A, a housing B, and a liquid-drug-dispensing portion C. Each element is explained with FIG. 2 in detail hereinafter.

The bladder assembly A is such a portion as storing or containing liquid drug therein and injecting liquid drug to a predetermined portion of human body, and comprises a rod-like inner shaft 1, a tubular outer shaft 2 slidably encasing the inner shaft 1, a bladder 3 placed outside the inner shaft 1 and outer shaft 2, and an inner shaft supporter 4 integrally formed with the inner shaft 1. A bell-shaped member 5 is fixed to one end of the outer shaft 2 on the opposite side from the inner shaft side. The bell-shaped member 5 can be formed integrally with the outer shaft 2. Though the inner shaft 1 is designed to slide inside the outer shaft 2, the inside of the outer shaft 2 is not required to function as a passage for liquid drug like the above-mentioned conventional liquid infusion device. Accordingly, it is preferable to make the clearance between the inner shaft 1 and outer shaft 2 as small as possible. For example, clearance of about 0.05 to 0.5 mm is preferable.

The inner shaft 1 and outer shaft 2 can be made of synthetic resin such as polycarbonate, polyethylene, and polypropylene. The bladder 3 can be made of elastic material such as silicone rubber, butyl rubber, nitryl butadiene rubber, poly-1,4-butadiene, polyisoprene, polyurethane, and butadiene stylene copolymer. The bladder 3 might employ a multilayer structure, which the present applicant formerly proposed (Japanese Patent Application No. 103510/1990), of a tubular body made of natural rubber and a silicone resin layer covering an inner surface of the tubular body.

The bladder 3 having a tubular shape is placed outside the inner shaft 1 and outer shaft 2 to cover these shafts. One end of the bladder 3 is airtightly fixed to the inner shaft 1 by sealing means 6 such as O-ring while the other end of the bladder 3 is similarly fixed to the outer shaft 2. The size and thickness of the bladder 3 are not particularly limited in the present invention, therefore, bladders having various kinds of size and thickness can be applied to a liquid infusion device of the present invention depending on the amount of liquid drug dispensed to patients, dispensation time and the like. The bladder is inflatable in both radial direction and longitudinal direction (i.e. axial direction of the inner shaft 1 and outer shaft 2) by the charging of liquid drug. The outer shaft 2 moves in the axial direction by the guiding of the inner shaft 1 with the movement of the bladder 3. An amount of liquid drug dispensed from the bladder 3 can be determined by marking with degrees at the surface of the inner shaft 1 or housing B, since the relationship between position of the outer shaft 2 and an amount of liquid drug remaining in the bladder 3 is constant.

A hydraulic pressure resistant filter 8 is provided at one end of the outer shaft 2 on the opposite side from the inner shaft side. The filter 8 serves to discharge air remaining in the bladder 3 when charging liquid drug into the bladder 3, and can be made of polyester, fluororesin, laminate of polyester and fluororesin, and the like. It is preferable that the filter allows the passage of ethylene oxide gas and the like used for sterilizing the inside of the bladder 3. The filter 8 is required to have hydraulic pressure resistance of at least 1.5 kg/cm$^2$, since the inner pressure of the bladder 3 increases to about 600 to 1000 mmHg when the charging of liquid drug is finished.

Figure 3:
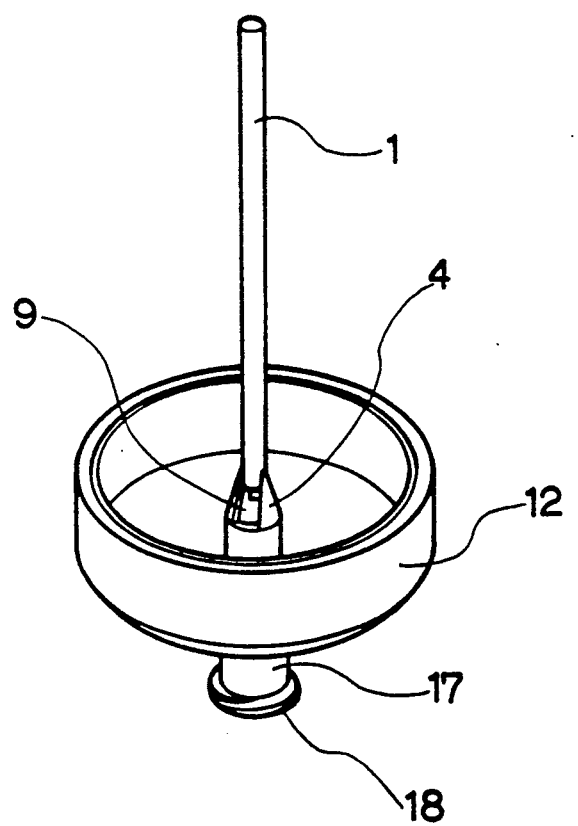
FIG. 3 is a perspective view of an inner shaft and an inner shaft supporter in the liquid infusion device of FIG. 1.

An inner shaft supporter 4 is integrally formed with the inner shaft 1 at one end thereof on the opposite side from the outer shaft side (refer to FIG. 3). The inner shaft supporter 4 comprises a short tubular member, and has at least one port 9 for charging and dispensing liquid drug at an end on the side of the inner shaft 1. The shape and number of the port 9 are not particularly limited in the present invention, and can be suitably determined in consideration of ease of flowing of liquid drug, strength of the inner shaft supporter 4, and the like. The port 9 communicates with an inlet/outlet portion of the housing B through the inside of the inner shaft supporter 4.

The housing B serves not only to prevent damage of the bladder 3 by the contact with external sharp objects but also to seal liquid drug so as not to disperse out when it leaks out from the bladder because of defects of the bladder such as pinholes. The housing B is preferably made of synthetic resin such as polyvinyl chloride, polypropylene, polycarbonate and ABS resin. The shape of the housing B is not limited in the present invention, and shape such as tubular or rectangular can be employed as long as the housing B contain the inflated bladder 3. If the outer diameter of the end on the opposite side of the inlet/outlet portion is reduced to form a tapered shape corresponding to a tapered shape of the bell-shaped member 5 of the outer shaft 2, the bell-shaped member 5 closely fits the inner surface of the housing when the charging of liquid drug is finished. In result, the bending of an inflated bladder and burst of the bladder due to vibration can be prevented. It is preferable that the housing B is made of transparent material to allow observation of liquid drug dispensed with naked eyes from outside the housing B. The size of the housing is determined depending on the size of the inflated bladder 3.

As described above, the housing B covers the bladder assembly A in a sealed condition to prevent leak-out of liquid drug even if the bladder 3 is damaged. There is arised a disadvantage, however, if the inside of the housing B is perfectly kept airtight, that air pressure in the housing B becomes high with the injection of liquid drug into the bladder 3 so that the injection of liquid drug beyond some volume becomes impossible. To avoid the above disadvantage, it is preferable to form an opening for air vent at a suitable place of the housing B and to provide hydrophobic filter, which allows passage of air but not liquid drug, at the opening. In the embodiment shown in FIG. 2, the opening 10 is formed at an end surface of the housing B. The hydrophobic filter 11 is so provided at the housing B as to cover the opening 10. When determining materials of the hydrophobic filter 11, it should be taken into consideration that liquid drug in the bladder 3 does not leak out from the housing B even if the bladder is damaged and air in the housing B is discharged with the inflation of the bladder 3 when liquid drug is injected into the bladder 3. Polyester, Teflon and the like are preferably employed.

One end surface of the housing B is closed with a cap 12. At a central portion of the cap 12, there is formed an inlet/outlet portion 13 for liquid drug which functions as a passage for liquid drug when charging liquid drug into the bladder 3 and injecting liquid drug in the bladder 3 into a predetermined portion.

A plug 14 is airtightly and liquidtightly inserted into the inlet/outlet portion 13 and is used for injecting liquid drug into the bladder. The plug 6 is made of rubber-like elastic material such as silicone rubber and has a superior prick resistance. In the specification the term "prick resistance" means a property which keeps liquid-tightness even if pricked with an injection needle many times, and which prevents the leak of liquid drug in the bladder. The plug 14 shown in FIG. 2 has a head 15. The head 15 engages with a projection 16 formed on the cap 12, and is designed to be fixed in the inlet/outlet portion 13. The fixation of the plug 14 can be carried out by adhesives.

Numeral 17 is a short tubular cap 17 for fixing a plug 14. A screwed portion 18 used for connecting a liquid-drug-dispensing portion stated below is formed at the periphery of an end of the cap 17.

The liquid-drug-dispensing portion C serves to deliver liquid drug dispensed from the bladder 3 to a device such as PSV (Periatric Skelton Vein) assembly and catheter. The liquid-drug-dispensing portion C comprises a tube 19 and a flow-regulating portion 20, and might include a mini clamp 21 and a connector 24 at need.

In the present embodiment, an injection needle 22 is attached to one end of the liquid-drug-dispensing portion C. By pricking the injection needle 22 into the plug 14, liquid drug charged in the bladder 3 beforehand is introduced toward the flow-regulating portion 20.

The connection between the housing B and liquid-drug-dispensing portion C can be carried out only by pricking the injection needle 22 into the plug 14. It is preferable, however, to use a connector 23 having a screwed portion inside thereof as shown in FIG. 1 and to screw the connector 23 with the fixation cap 17 from a viewpoint of secure connection. It is, of course, possible to employ connecting methods such as engagement connection besides screw connection.

The flow-regulating portion 20 serves to regulate flow rate of liquid drug. As a flow-regulating portion, there can be employed (1) a pipe, of which end portion is closed, having at least one small hole, (2) a pipe having small holes such as porous glass pipe, which were proposed by the present applicant in Japanese Unexamined Patent Publication No. 135360/1989 (Japanese Patent Application No. 294809/1987), and (3) a pipe having a very small inner diameter which was proposed by the present applicant in Japanese Unexamined Patent Publication No. 11160/1990 (Japanese Patent Application No. 162271/1988).

A tube 19 for dispensing liquid drug made of soft synthetic resin such as soft polyvinyl chloride, polypropylene and polyethylene is connected to the flow-regulating portion 20. In FIG. 1, the flow-regulating portion 20 is arranged at the injection needle 22 side, but it might be arranged at the connector 24 side. The inner diameter, thickness and length of the tube 19 might be determined in consideration of an amount of liquid drug or use of a liquid infusion device. When a mini clamp 21 is provided at a midway section of the tube 19, the dispensation of liquid drug can be easily stopped or reopened. A tapered connector 24 is attached to the end of the tube 19. Through the connector 24, vein needle or PSV assembly is connected to the tube 19. A check valve (not shown) might be mounted in the connector to prevent a back flow of liquid drug due to vein or artery pressure.

Next, there is explained a use of the embodiment of a liquid infusion device of the present invention.

The injection of liquid drug into the bladder 3 is carried out by inserting an injection needle of an injector and the like (not shown) into the inlet/outlet portion 13 and pricking the plug 14 with the injection needle. With the charging of liquid drug, the bladder 3 inflates in its radial direction and axial direction. In that case, air remaining in the bladder 3 is discharged outside through the hydraulic pressure resistant filter 8. Further, with the inflation of the bladder 3, the outer shaft 2 closely encasing the inner shaft 1 slides in the longitudinal direction, and moves along the inner surface of the housing B. After a predetermined amount of liquid drug is charged into the bladder 3, the injector is pulled out from the plug 14. When the charging of liquid drug into the bladder 3 is finished, the bell-shaped member 5 closely fits the inner surface of the housing B, so that the bending of the inflated bladder 3 and burst of the bladder 3 due to vibration are prevented.

Next the plug 14 is pricked with the needle 22 of liquid-drug-dispensing portion C. In that case, the mini clamp 21 is required to be closed so as to prevent back flow of liquid drug toward the tube 19. Then, the liquid infusion device is connected, through the connector 24, to a PSV assembly or a bladder catheter according to portions of human body to be dispensed with liquid drug. The dispensation of liquid drug into human body of a patient is carried out after a prescribed operation such as air venting.

Next, there is explained another embodiment of a liquid infusion device of the present invention.

Figure 4:
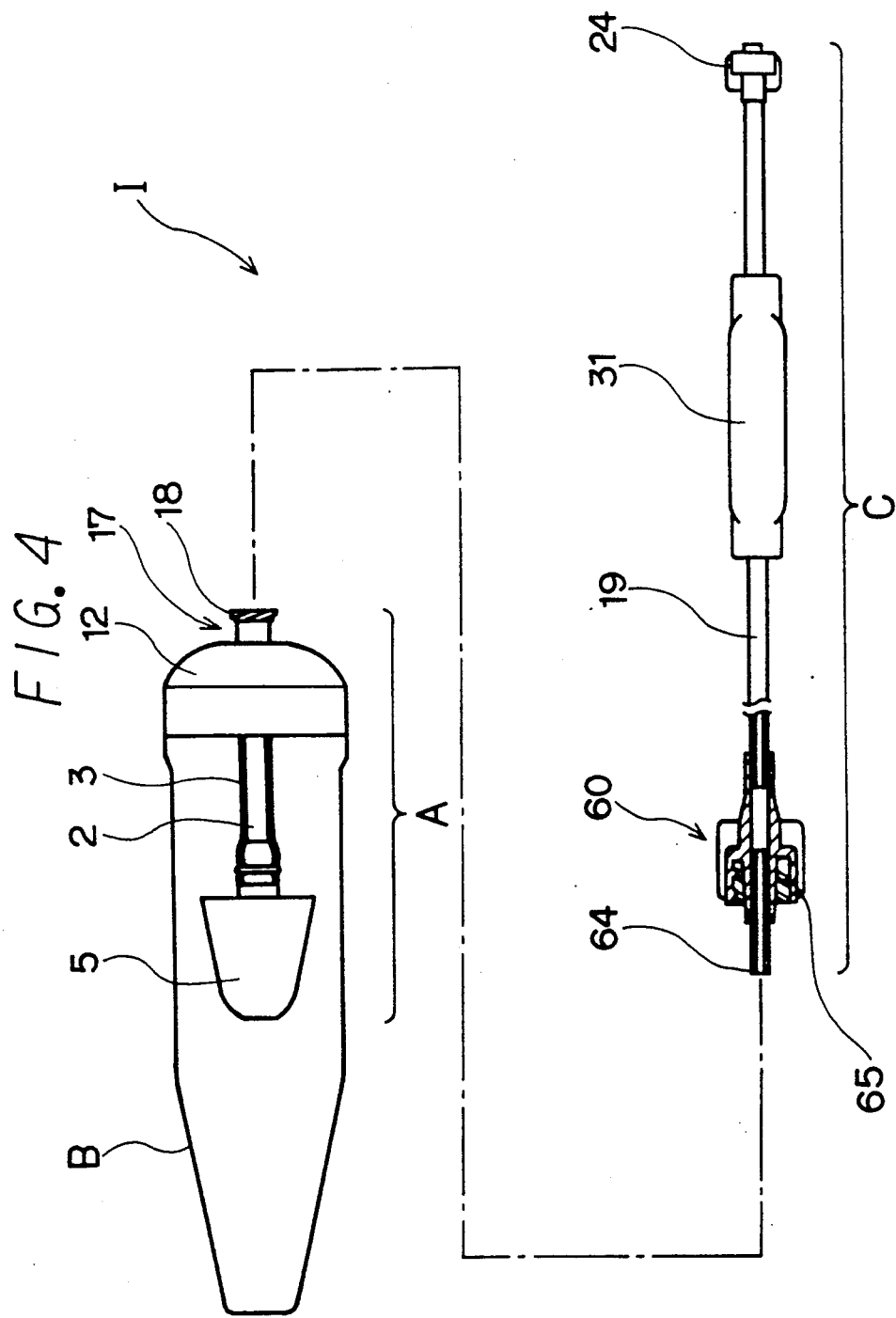
FIG. 4 is an explantory view of another embodiment of a liquid infusion device of the present invention wherein a bladder assembly is not connected to a liquid-drug-dispensing portion.

FIG. 4 is an explanatory view of another embodiment of a liquid infusion device of the present invention. The device shown in FIG. 4 differs from that shown in FIGS. 1 to 3 in the connection structure between a bladder assembly and a liquid-drug-dispensing portion.

Figure 2:
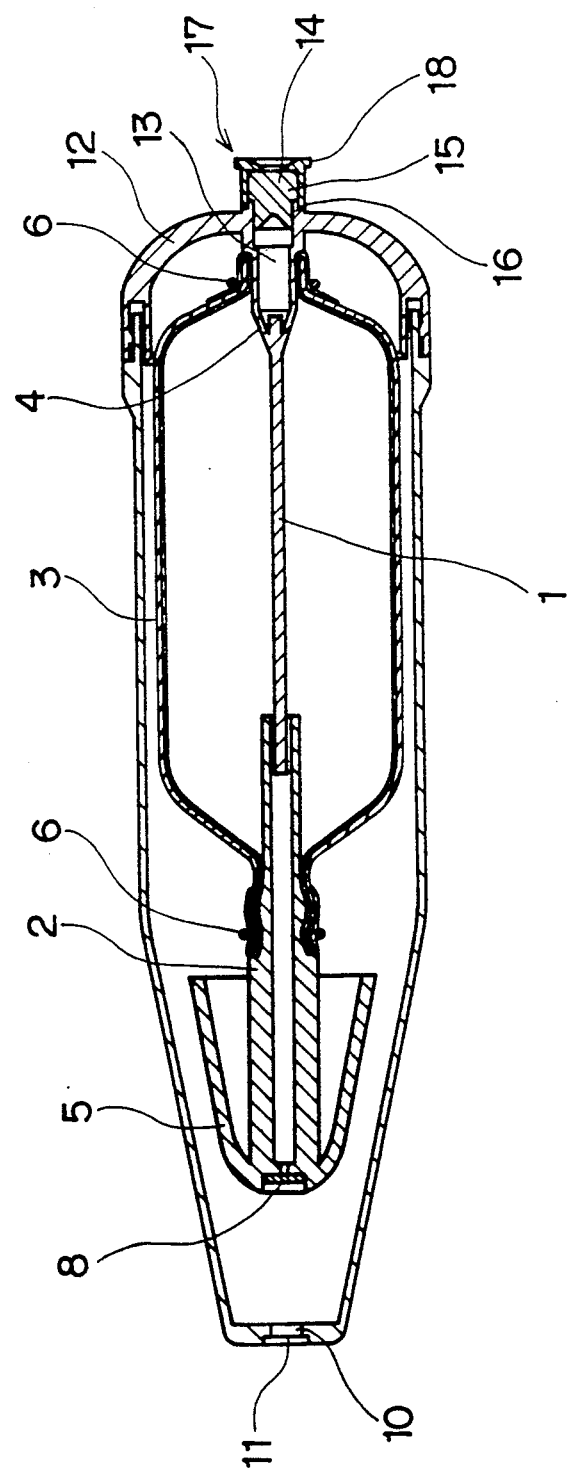
FIG. 2 is an enlarged sectional view of a bladder assembly of the liquid infusion device of FIG. 1 wherein liquid drug is charged into a bladder.

That is, in the embodiment shown in FIGS. 1 to 3, a needle is pricked into a plug made of rubber-like elastic material, and the charging and dispensation of liquid drug are carried out through the needle. Since the charging of liquid drug is carried out through a needle having a narrow passage, the charging pressure becomes high so that the charging becomes difficult and requires much time. Further, it is not easy to prick the needle into the plug straight, so that there is a problem that liquid drug leak out from a clearance between the needle and plug when dispensing liquid drug into human body for a long period of time.

The above-mentioned drawback is perfectly avoided in the case of the embodiment shown in FIG. 4, since the embodiment of FIG. 4 employs a check valve. That is, in the embodiment of FIG. 4, an open side end of an inlet/outlet portion for charging liquid drug into a bladder and dispensing liquid drug in the bladder is so formed as to allow engagement connection or screw connection. Further, in the inlet/outlet portion, there is provided a check valve. Liquid drug charged in the bladder cannot flow back by a communicating pipe, a hub of syringe, since a tip 70 of the hub does not come to the inlet of the check valve. As a result, liquid drug can be charged into the bladder by directly engaging or screwing a syringe containing liquid drug with the above-mentioned connecting end. In that case, liquid drug charged in the bladder does not flow back, since the check valve is provided in the inlet/outlet portion.

The liquid-drug-dispensing portion has an engage-type or screw-type connector with a communicating tube which has sufficient length to communicate with the inside of the bladder and open the check value. When the connector is connected to an engage-type or screw-type connecting portion of the bladder assembly, the above-mentioned communicating pipe pushes and opens the check valve from a liquid-drug-charging direction, so that the function of the check valve is released. Thus, liquid drug can be dispensed without using a conventional injection needle.

Figure 5:
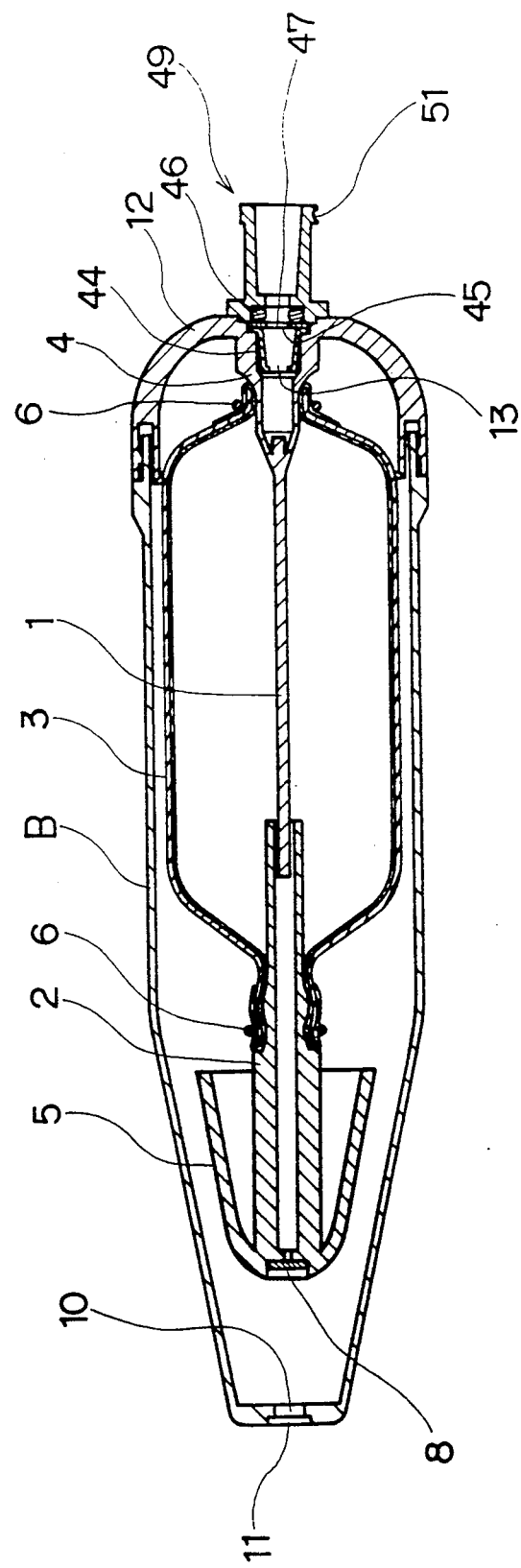
FIG. 5 is an enlarged sectional view of a bladder assembly of the liquid infusion device of FIG. 4 wherein liquid drug is charged into a bladder.

Next, details of another embodiment of the present invention shown in FIGS. 4 to 5 are explained. Explanations for such elements that are common to those in the embodiment of FIGS. 1 to 3 are omitted.

One end surface of the housing B is closed with a cap 12. At a central portion of the cap 12, there is formed an inlet/outlet portion 13 for liquid drug which functions as a passage for liquid drug when charging liquid drug into the bladder 3 and injecting liquid drug in the bladder 3 into a predetermined portion of human body.

In the inlet/outlet portion 13, there are provided a duck-bill-type check valve 44, a fixed disc 45, and a sealing means 46 in this order from the bladder 3. A closed end of the duck-bill-type check valve 44 has a pointed or sharp configuration like a bill of a platypus. The check valve 44 allows flow of liquid drug into the bladder 3 while prevents back flow of charged liquid drug. As a check valve in the present embodiment, there can be used a parasol valve, a flap valve, a poppet valve, a ball valve and the like besides the above-mentioned duck-bill-type valve. Examples of material for the valve are, for instance, fluororesin, nylon resin, polyolefine, polyvinyl chloride, polycarbonate, and silicone resin. The fixed disc 45 supports a base plate of the check valve 44. At a central portion of the fixed disc 45, an opening 47 for passage of liquid drug is formed.

Figure 6:
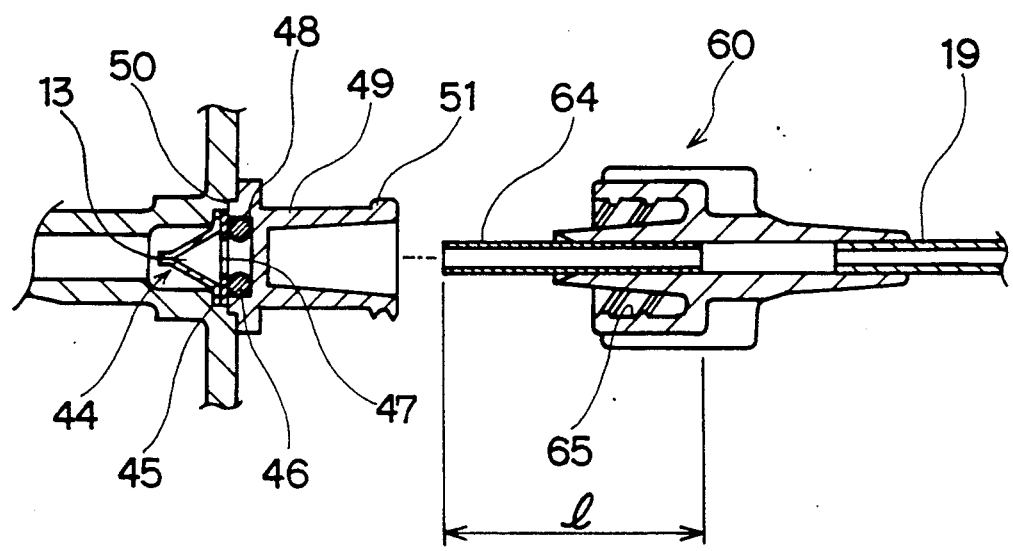
FIG. 6 is an enlarged sectional view of a connector of the liquid-drug-dispensing portion and a Leur-tapered adapter of a housing of FIG. 4.

In FIG. 6, an O-ring as a sealing means 46 is placed in an annular recess 48 defined by a lock adapter stated below and the fixed disc 45. The inner diameter of the O-ring is designed to be equal to or a little smaller than the outer diameter of a communicating pipe, so that sealing property when the communicating pipe is inserted into the inlet/outlet portion 13 is improved or advanced.

Numeral 49 is an approximately tubular lock adapter of which the inner surface is formed to be Leur-tapered. The lock adapter 49 is put in a recess 50 formed on the cap 12. A screwed portion 51 used for connecting a liquid-drug-dispensing portion is formed at the periphery of an end of the lock adapter 49. Besides the screwed portion 51, an engage-type connecting means can be used.

The liquid-drug-dispensing portion C comprises a connector 60 to be connected to the lock adapter 49, a flow-regulating portion 31 for regulating flow rate of liquid drug, a tube 19 for dispensing liquid drug, and a connector 24.

Figure 7:
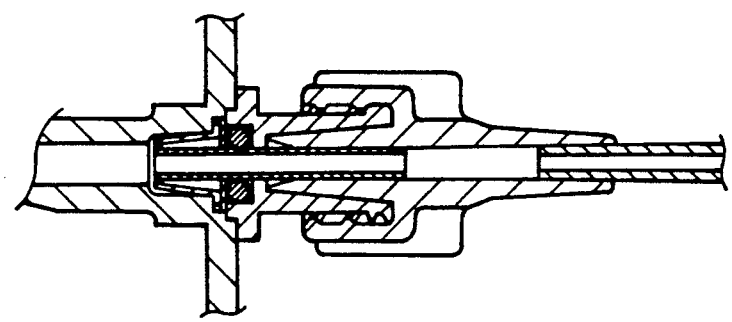
FIG. 7 is an explanatory view showing the state wherein the connector of FIG. 6 is inserted into the Leur-tapered adapter of FIG. 6.

At one end of the connector 60, there is provided a communicating pipe 64 having sufficient length to open the check valve 44 and to communicate with the inside of the bladder 3 when the connector 60 is connected to the lock adapter 49. The communicating pipe 64 can be made of synthetic resin such as polycarbonate, polyvinyl chloride and polyolefin, or metal such as stainless steel. In the present embodiment, the communicating pipe 64 is adhered to the inner surface of the connector 60. As stated above, a projecting length l of the communicating pipe 64 is so designed as to open the duck-bill-type check valve 44 when the connector 60 is connected to the lock-adapter, as shown in FIG. 7. As a result, the checking function of the check valve 44 is compulsorily released, so that liquid drug charged in the bladder 3 can be dispensed without using an injection needle.

Numeral 65 is a screwed portion of the connector 60. The bladder assembly A and liquid-drug-dispensing portion C are connected to each other by the screwed portion 65 and the screwed portion 51 formed on the lock adapter 49. Connection can be carried out by engagement connection besides screw connection.

Next, there is explained a use of the present embodiment.

Figure 8:
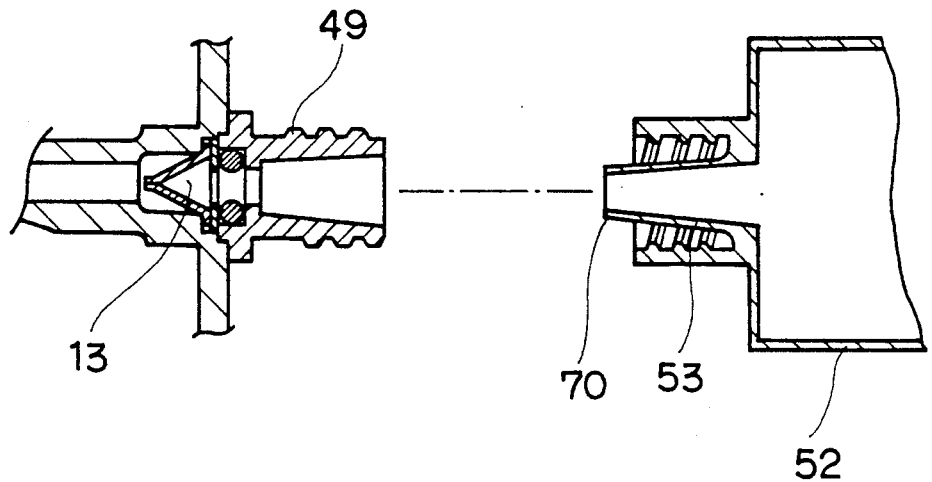
FIG. 8 is an explanatory view of the state wherein a syringe is not connected to the housing.
Figure 9:
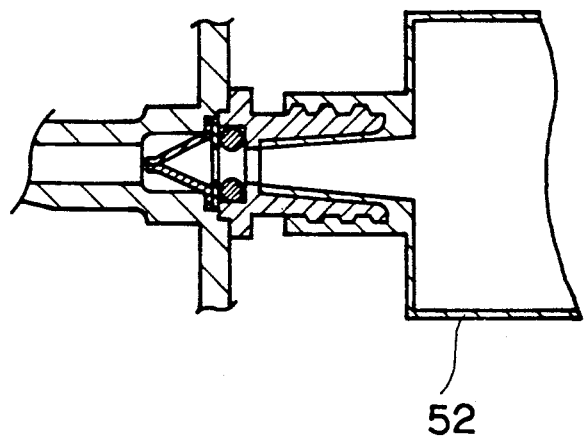
FIG. 9 is an explanatory view of the state wherein liquid drug is charged into a bladder.
Figure 10:
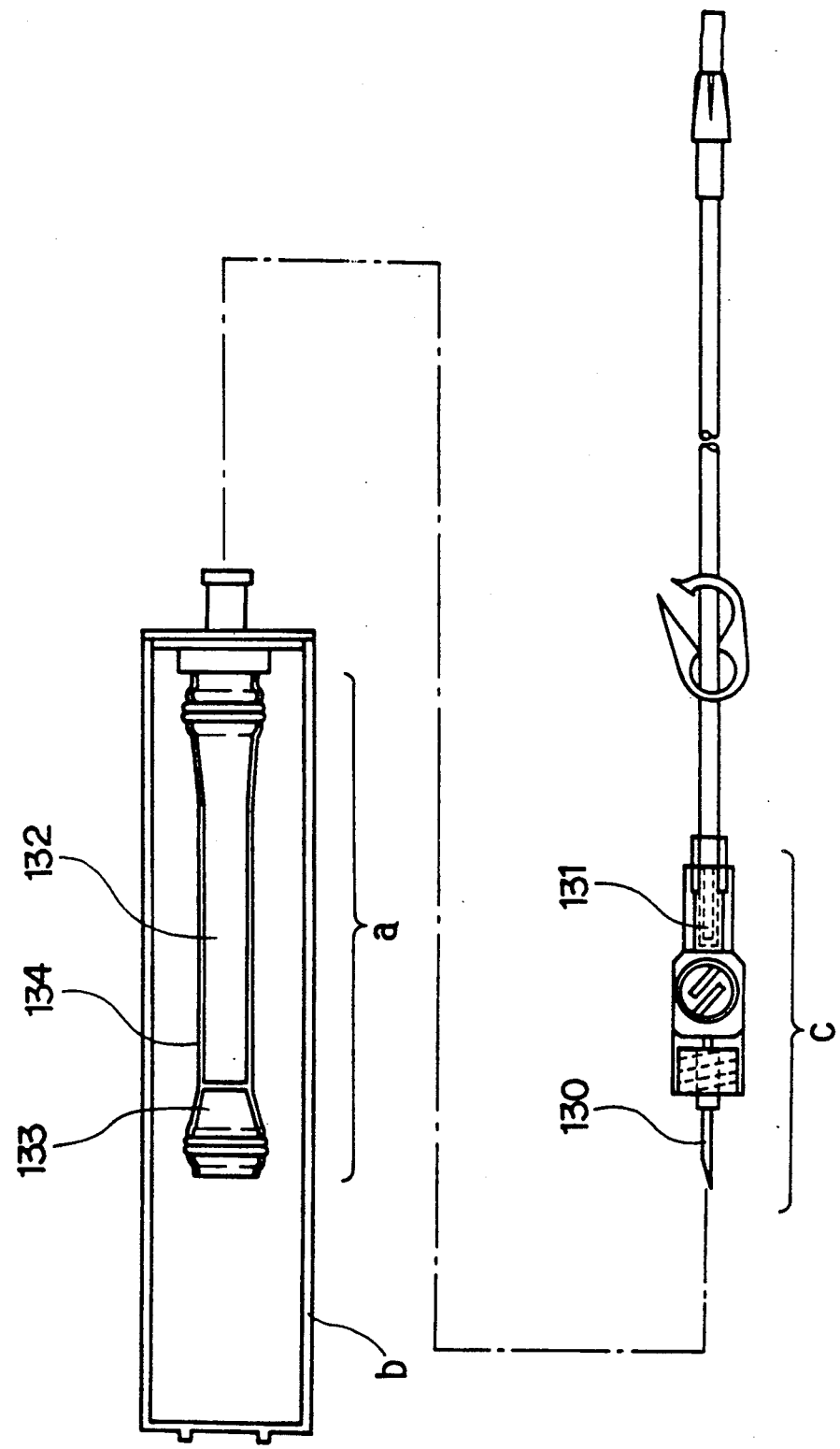
FIG. 10 is an explanatory view of a conventional liquid infusion device wherein an injection needle is not pricked into an injection plug.
Figure 11:
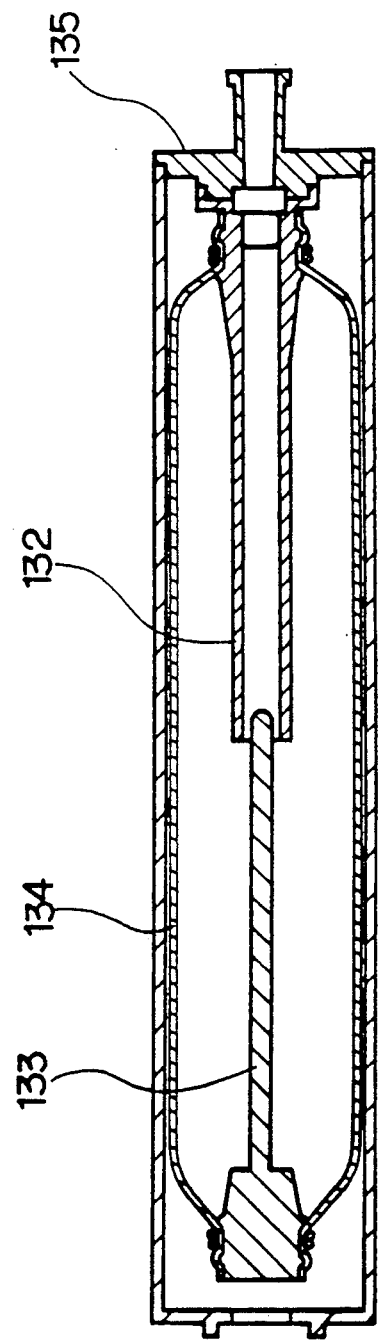
FIG. 11 is an enlarged sectional view of a bladder assembly of the liquid infusion device of FIG. 10 wherein liquid drug is charged into a bladder.

The charging of liquid drug into a bladder is carried out, as shown in FIGS. 8 to 9, by inserting a hub 53 of syringe 52 into an inlet/outlet portion 13 with pushing the hub 53 onto the Leur-tapered inner surface of the lock adapter 49. In that case, a tip of a hub 53 of the syringe 52 stays on the inlet side of the check valve 44. A screw-type connector can be used besides a Leur-tapered engage-type connector. The charging pressure is reduced in comparison with a conventional injecting needle according to a widened injection opening, so that the charging operation becomes easy and can be finished in a short time.

Next, the dispensing of liquid drug in a bladder is carried out, as shown in FIGS. 6 to 7, by inserting a tip of the communicating pipe 64 into the inside of the bladder 3 to open the check valve 44.

The connector 60 of the liquid-drug-dispensing portion C is connected to the lock adapter 49. As a result, the communicating pipe 64 of the connector 60 pushes and opens the check valve 44, thereby the communicating pipe 64 communicates with the inside of the bladder 3.

Then, the liquid infusion device is connected, through the connector, to a PSV assembly or a bladder catheter according to portions of human body to be dispensed with liquid drug. The dispensation of liquid drug into human body of a patient is carried out after a prescribed operation such as air venting.

As explained above, according to the liquid infusion device of the present inveniton, there is formed at least one port for liquid drug at a root of an inner shaft to charge or dispense liquid drug through the port. Accordingly, a clearance between the inner shaft and outer shaft can be determined in consideration of only slidability between two shafts, and can be made very small. As a result, an amount of liquid drug remaining in the bladder can be greatly reduced in comparison with conventional liquid infusion devices.

Further, when a check valve is provided in an inlet/outlet portion and a bladder assembly is connected to a liquid-drug-dispensing portion by engage-type connection or screw-type connection, use of a needle can be omitted on charging liquid drug into the bladder. Accordingly, the charging pressure on charging liquid drug can be reduced, so that the charging of liquid drug can be finished easily and in a short time. The use of needle can be omitted also in dispensing liquid drug.

What is claimed is:

1. A liquid infusion device comprising
(a) a bladder assembly comprising a an inner shaft, a tubular outer shaft slidably encasing the inner shaft, an inner shaft supporter integrally formed with the inner shaft at one end of the inner shaft on the opposite side from the outer shaft side, and a bladder made of elastic material and placed outside the outer shaft and inner shaft wherein one end of the bladder is tightly fixed to the outer shaft and the other end of the bladder is tightly fixed to the inner shaft, (b) an approximately tubular housing containing the bladder assembly and having an inlet/outlet portion of liquid drug at an end of the housing, (c) a liquid-drug-dispensing portion connected to the inlet/outlet portion and having a flow-regulating portion for regulating a flow rate of liquid drug wherein the inner shaft supporter has at least one port for liquid drug communicating with the inlet/outlet portion.

2. The device of claim 1, wherein a plug for injecting liquid drug is provided in the inlet/outlet portion, and the liquid-drug-dispensing portion has at one end thereof an injection needle to be sticked into the plug.

3. The device of any one of claims 1 or 2, wherein a hydraulic pressure resistant filter is provided at one end of the outer shaft on the opposite side from the inner shaft side.

4. The device of any one of claims 1 or 2, wherein an outer diameter of an end of the housing opposite to the inlet/outlet portion is reduced to form a tapered shape, a bell-shaped-member having a tapered shape corresponding to the tapered shape of the housing is formed at one end of the outer shaft on the opposite side from the inner shaft side.

5. The device of claim 1, wherein an engaging connector is provided at an open side end of the inlet/outlet portion, a check valve preventing back flow of liquid drug in the bladder on charging liquid drug into the bladder and capable of opening, on dispensing liquid drug in the bladder, by a communicating pipe inserted from the open side end of the inlet/outlet portion is provided in the inlet/outlet portion, and an engaging connector with a communicating pipe having sufficient length to communicate with the inside of the bladder is formed at one end of the liquid-drug-dispensing portion.

6. The device of claim 1, wherein a screw connector is provided at an open side end of the inlet/outlet portion, a check valve preventing back flow of liquid drug in the bladder on charging liquid drug into the bladder and capable of opening, on dispensing liquid drug in the bladder, by a communicating pipe inserted from the open side end of the inlet/outlet portion is provided in the inlet/outlet portion, and a screw connector with a communicating pipe having sufficient length to communicate with the inside of the bladder is formed at one end of the liquid-drug-dispensing portion.

* * * * *